(12) United States Patent
Bowman

(10) Patent No.: US 6,882,413 B2
(45) Date of Patent: Apr. 19, 2005

(54) ROTATING HEAD ELLIPSOMETER

(75) Inventor: Barry R. Bowman, Dublin, CA (US)

(73) Assignee: Therma-Wave, Inc., Fremont, CA (US)

( * ) Notice: Subject to any disclaimer, the term of this patent is extended or adjusted under 35 U.S.C. 154(b) by 339 days.

(21) Appl. No.: 10/144,288

(22) Filed: May 13, 2002

(65) Prior Publication Data

US 2003/0147076 A1 Aug. 7, 2003

Related U.S. Application Data

(60) Provisional application No. 60/354,387, filed on Feb. 4, 2002.

(51) Int. Cl.[7] .............................................. G01N 21/00
(52) U.S. Cl. ............................... 356/237.2; 356/237.5; 356/237.6
(58) Field of Search ............................ 356/369, 368, 356/367, 370, 364, 237.4, 237.3, 445, 237.6, 448, 237.1, 237.2

(56) References Cited

U.S. PATENT DOCUMENTS

| | | | |
|---|---|---|---|
| 3,858,983 A | 1/1975 | Foster et al. ................. | 356/163 |
| 4,745,526 A | 5/1988 | Sestak .......................... | 362/35 |
| 4,933,567 A * | 6/1990 | Silva et al. ............. | 250/559.09 |
| 5,042,951 A | 8/1991 | Gold et al. .................. | 356/369 |
| 5,076,696 A * | 12/1991 | Cohn et al. .................. | 356/369 |
| 5,329,357 A | 7/1994 | Bernoux et al. ............. | 356/369 |
| 5,432,607 A * | 7/1995 | Taubenblatt ................ | 356/364 |
| 5,608,526 A | 3/1997 | Piwonka-Corle et al. ... | 356/369 |
| 5,726,756 A | 3/1998 | Aki et al. ..................... | 356/381 |
| 5,867,276 A | 2/1999 | McNeil et al. ............... | 356/445 |
| 5,910,842 A | 6/1999 | Piwonka-Corle et al. ... | 356/369 |
| 5,995,218 A | 11/1999 | Ide ........................... | 356/237.1 |
| 6,020,957 A * | 2/2000 | Rosengaus et al. ...... | 356/237.4 |
| 6,031,614 A * | 2/2000 | Michaelis et al. .......... | 356/369 |
| 6,038,026 A | 3/2000 | Maris ......................... | 356/357 |
| 6,297,880 B1 | 10/2001 | Rosencwaig et al. ....... | 356/369 |

(Continued)

FOREIGN PATENT DOCUMENTS

| | | | |
|---|---|---|---|
| EP | 0 816 926 A3 | 5/1999 | ............. G03F/7/20 |
| JP | 58034310 | 2/1983 | ........... G01B/11/30 |
| JP | 05060527 | 3/1993 | ........... G01B/11/24 |
| JP | 08190066 | 7/1996 | ........... G02B/26/10 |
| JP | 09138364 | 5/1997 | ........... G02B/26/10 |
| JP | 10300861 | 11/1998 | ........... G01W/1/14 |
| JP | 11295785 | 10/1999 | ........... G03B/15/02 |
| JP | 2001305071 | 10/2001 | ......... G01N/21/956 |
| WO | WO 99/02970 | 1/1999 | .......... G01N/21/21 |
| WO | WO 00/02037 | 1/2000 | .......... G01N/21/88 |
| WO | WO 02/079760 A2 | 10/2002 | .......... G01N/21/21 |

OTHER PUBLICATIONS

IBM Technical Disclosure Bulletin, "Automated, Remote, Programmable, Ellipsometer Drive Mechanism," vol. 31, No. 9, Feb. 1989, pp. 108–113.
IBM Technical Disclosure Bulletin, "Automated Multiple Angle of Incidence Ellipsometer System," vol. 32, No. 9A, Feb. 1990, pp. 417–424.
S.A. Coulombe et al., "Ellipsometric–Scatterometery for sub–0.1 $\mu$m /CD measurements," *SPIE*, vol. 3332, 1998, pp. 282–293.

*Primary Examiner*—Layla Lauchman
(74) *Attorney, Agent, or Firm*—Stallman & Pollock LLP

(57) ABSTRACT

An ellipsometric apparatus provides a rotating focused probe beam directed to impinge a sample in any direction. A rotating stage rotates the wafer into a linear travel range defined by a single linear axis of a single linear stage. As a result, an entire wafer is accessed for measurement with the single linear stage having a travel range of only half the wafer diameter. The reduced single linear travel results in a small travel envelope occupied by the wafer and consequently in a small footprint of the apparatus. The use of a rotating probe beam permits measurement of periodic structures along a preferred direction while permitting the use of a single reduced motion stage.

40 Claims, 10 Drawing Sheets

U.S. PATENT DOCUMENTS

| | | | |
|---|---|---|---|
| 6,320,609 B1 * | 11/2001 | Buchanan et al. | 348/126 |
| 6,362,881 B1 | 3/2002 | Pickering et al. | 356/369 |
| 6,423,977 B1 | 7/2002 | Hayasaki et al. | 250/559.19 |
| 6,473,186 B1 | 10/2002 | Kawasaki et al. | 356/512 |
| 6,493,064 B1 | 12/2002 | Cabiri et al. | 355/53 |
| 6,507,394 B1 | 1/2003 | Cheng et al. | 356/237.5 |
| 6,778,273 B1 * | 8/2004 | Norton et al. | 356/364 |
| 2002/0018217 A1 | 2/2002 | Weber-Grabau et al. | 356/601 |
| 2003/0020912 A1 * | 1/2003 | Norton et al. | 356/369 |
| 2003/0030806 A1 * | 2/2003 | Ebert et al. | 356/369 |

\* cited by examiner

ROTATING HEAD ELLIPSOMETER

PRIORITY

This application claims priority to provisional application Ser. No. 60/354,387, filed Feb. 4, 2002, the disclosure of which is incorporated herein by reference.

FIELD OF INVENTION

The present invention relates to ellipsometric systems for measuring feature configurations on wafers. Particularly, the present invention relates to a compact ellipsometer useful for measuring features that have a preferential measurement direction.

BACKGROUND OF THE INVENTION

Semiconductors are typically fabricated by depositing and etching a number of layers that are shaped and configured on the upper or top surface of a wafer. Controlling those fabrication steps and testing the wafer early during production helps to keep production costs low. An increasingly important technique for a non-destructive measurement of semiconductors is ellipsometry. In ellipsometry, a specifically configured and focused probe light beam is directed to reflect off the wafer. The change in polarization state of the beam induced by the interaction with the wafer is monitored to provide information about the wafer.

Ellipsometers have been used extensively to monitor thin film parameters such as thickness, index of refraction and extinction coefficient. More recently, ellipsometers have been used to monitor small, repeating, periodic structures (critical dimensions) on wafers. These periodic structures are similar to a grating and the measured data can be subjected to a scatterometry analysis to derive information about the structure. Information of interest includes line width and spacing as well as side wall profile.

Such periodic structures have distinct orientations. It has been found that the useful information about such structures can be obtained if the probe beam of the ellipsometer is directed substantially perpendicular to the line structure.

As seen in FIG. 1, a typical wafer W will have multiple such periodic structures PS1, PS2 formed thereon. In some case, all of the periodic structures will be oriented in the same direction (i.e. all lines parallel). In other cases, some of the structures will have lines running perpendicular to other structures.

A conventional, stand-alone ellipsometer is typically provided with a stage for moving the wafer through full linear motions FX, FY as well as rotation about the central axis so that the probe beam PB can be directed to each of the periodic structures PS1, PS2 in the appropriate direction (usually perpendicular to the line structure). The linear motions FX, FY are about equal to the wafer diameter WD. The wafer W moved during the measurement of it consequently occupies a travel envelope LE that extends in direction of the linear axis of about twice the wafer diameter. The travel envelope LE influences mainly the minimal footprint of an ellipsometer apparatus.

Recently, there has been a push to substantially reduce the size of ellipsometer apparatus. This effort is particularly directed to allowing an ellipsometer to be incorporated directly into a semiconductor processing tool. To achieve the desired miniaturization, stage systems have been developed which reduce the total range of motion of the wafer, thereby reducing the travel envelope and consequently the footprint of the system. The use of these stages has not impeded the measurement of thin film parameters on non-patterned measurement areas since such measurements are not effected by the direction in which the probe beam strikes the sample. However, such reduced motion stage systems have caused a problem with measuring periodic structures where the impinging direction of the probe beam PB has to correspond to a measurement orientation of the periodic structures PS1, PS2.

This difficulty can best be seen in FIGS. 2A and 2B. In FIG. 2A, the probe beam PB is shown striking periodic structure PS1 perpendicular to the line structure. When the operator wishes to measure periodic structure PS2, the rotating stage is used to bring the sector of the wafer where that structure is located within the region which can be reached by the probe beam. As noted above, the stage travel in the X and Y directions is not sufficient to bring the structure PS2 under the probe beam without a rotation. Unfortunately, and as seen in FIG. 2B, the result of this rotation is to orient the periodic structure PS2 so that the probe beam impinges thereon in a direction parallel to the lines. As noted above, it has been found that relevant information can be obtained when the beam strikes the structure perpendicular to the line structure.

Accordingly, it would be desirable to develop an ellipsometer system, which can utilize a reduced motion stage but also provides for optimal measurement of both thin film parameters and periodic structures.

SUMMARY

An ellipsometric apparatus has a rotating optics plate on which a measurement unit is assembled that performs reflectance measurements of features fabricated on a wafer. The measurement unit is preferably an optical assembly that performs well known directional reflectance measurements (for example, reflectometry and ellipsometry) with a probe beam impinging the surface features in a predetermined impinging direction. In the illustrated embodiment, a broadband rotating compensator (waveplate retarder) system is provided by the optical assembly. Such a system is disclosed in U.S. Pat. No. 5,973,787. A suitable rotating analyzer system is shown in U.S. Pat. No. 5,608,526. See also, U.S. Pat. No. 6,278,519. All of the above patents are incorporated herein by reference.

Rotating the optical assembly allows the probe beam to be directed to the sample from various directions. In the preferred embodiment, the focus spot of the probe beam is essentially coaxial with the revolution axis of the optical assembly, which itself is essentially normal to the wafer surface. As a result, by rotating the optical assembly any surface feature placed within the focus spot may be impinged by the probe beam in any impinging direction.

For a directional reflectance measurement, a sample wafer is fixed within the apparatus on a rotating stage that itself is moved by a single linear stage along a linear travel range. The rotating stage and the linear stage are correspondingly operated by a processor such that any measurement area of the wafer may be brought within the focal spot. In the preferred embodiment, the linear travel range is about half the wafer diameter and a rotating range of the rotating stage is at least 360°. The invention can also be applied to the use of ½X, ½Y, theta stage systems.

The combined rotational and linear positioning movement induced on the wafer results in a varying measurement orientation of the surface features within the focal spot. The processor controls the orientation of the rotating optics plate such that the impinging direction corresponds to the measurement orientation.

Limiting the linear travel to only a single linear axis with a travel range of about half the wafer diameter significantly reduces a travel envelope that the measured wafer occupies within the apparatus. The reduced travel envelope again provides for a reduced footprint of the apparatus itself.

A number of directional reflectance measurements may be performed during a measurement cycle of a wafer. Since every reposition of the wafer requires a repositioning of the rotating optics plate, the entire optical assembly needs to be angularly accelerated and decelerated in a short period so that the entire wafer measurement may be accomplished in a feasible period. Since the masses involved in rotating the optics plate are significantly larger than the masses involved in positioning the wafer, a driver motor is specifically configured for driving the rotating optics plate and the optical assembly with a relatively high torque compared to those of the other driver motors involved in positioning the wafer.

Geometric constrains of the optical assembly require the rotating optics plate to remain within a certain height above the rotating stage. On the other hand, the rotating optics plate has a minimal thickness and a stiffness sufficient for precisely holding the individual elements of the optical assembly regardless of the forces induced on them during their acceleration and deceleration. Also, a certain gap height between the rotating stage and the bottom of the rotating optics plate is maintained for loading and unloading the wafer. In conjunction with this dimensional constrains and stiffness requirements, the driver motor is configured in order to consume minimal space, while providing highly accurate positioning with a high torque and low energy consumption. The driver motor is preferably a low profile ring motor embedded in the periphery of the rotating optics plate. A stator of the driver motor is attached at an immobile portion of the apparatus top whereas a rotor of the driver motor is attached to the rotating optics plate.

The rotating optics plate has a central opening within which optical elements for providing and capturing the impinging and reflected beams are assembled in direct proximity to the wafer surface. The driver motor has a ring shape that fits around the central opening. At the same time, the ring shape provides a high ratio of torque to magnetic force compared to that of a conventional driver motor. The high ratio provides for a low energy consumption of the motor, which in turn assists in keeping the thermal load induced during the operational use of the motor low. In addition, the ring design reduces and broadens a thermal path for evenly channeling the thermal energy from stator coils onto the immovable portion of the apparatus top.

An outside diameter of the motor is limited by the width of the apparatus. In order for the driver motor to fit within the available space defined by the height requirements of the optical assembly and the rotating optics plate, the driver motor has a relatively small height compared to the radial extension of its ring section.

In the preferred embodiment, the motor directly drives the rotating optics plate without any reduction gear. The positioning is consequently accomplished with highest precision while the over all design of the components involved in rotating the optical assembly are kept simple and in a low number.

The combination of a single linear stage, a specifically configured ring motor and a directly driven, rotating optical assembly provides for an ellipsometry apparatus that has a minimum foot print for a given wafer size.

The subject invention allows periodic structures to be measured from a preferred direction while using a reduced motion stage. It should also be noted that this system allows any measurement area to be measured from any direction. While it is generally true that maximum information may be obtained when measuring a periodic structure when the beam is directed perpendicular to the line structure, additional information can be obtained from measurements where the beam is directed parallel to the line structure or even at a 45 degree angle with respect thereto. The subject invention would allow measurements from any desired direction. Such measurements could be used individually or combined in a regression analysis to more fully characterize the structure.

BRIEF DESCRIPTION OF THE FIGURES

FIG. 5 exemplary illustrates the spatial relations of the individually moving units within the apparatus.

DETAILED DESCRIPTION

Overview

Figure 3:
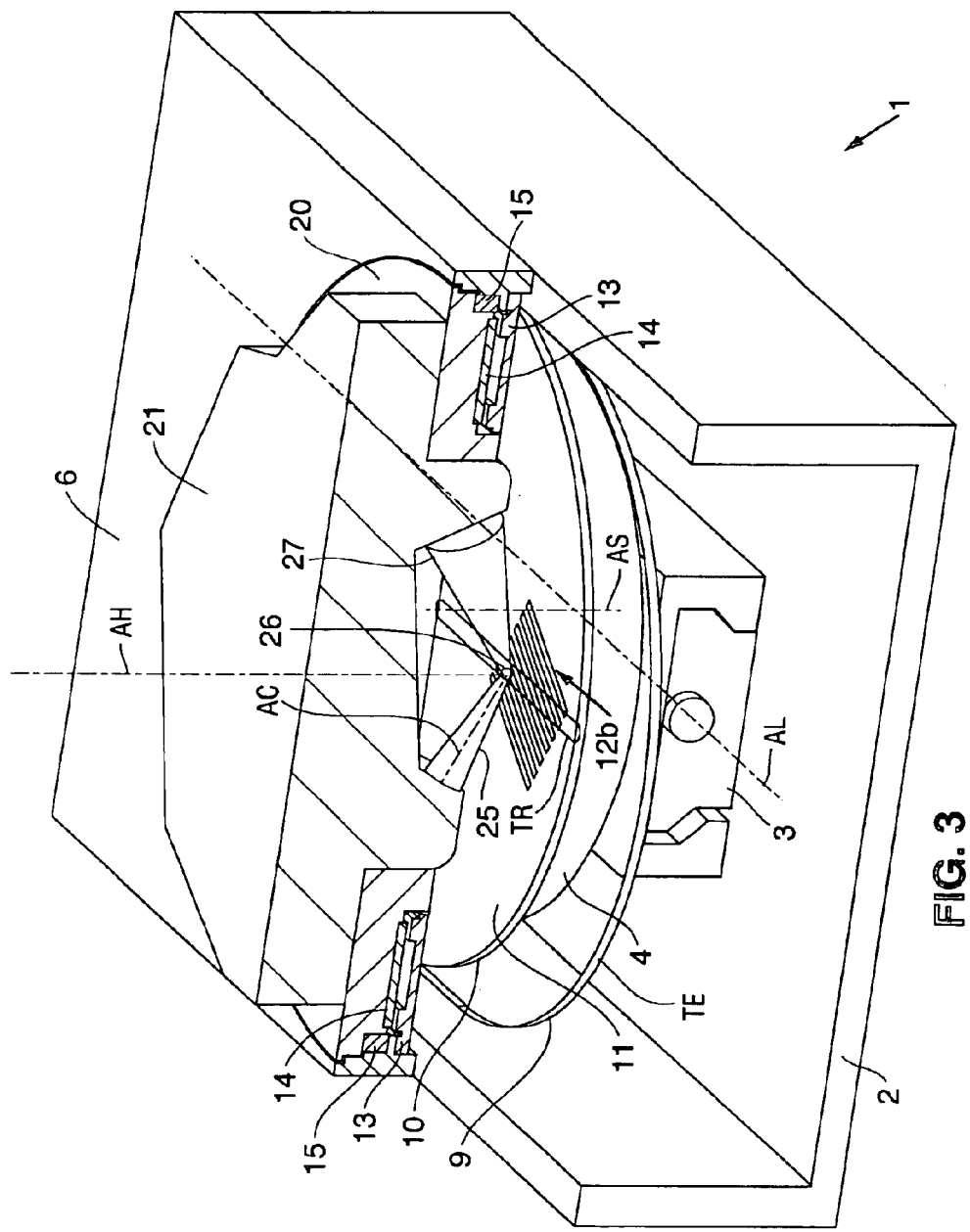
FIG. 3 shows a simplified perspective view of an exemplary apparatus having a rotating optics plate. The top portion of the apparatus is illustrated as section view cut along a plane parallel to a beam plane defined by a center of a probe beam and an axis of revolution of the rotating optics plate.
Figure 4:
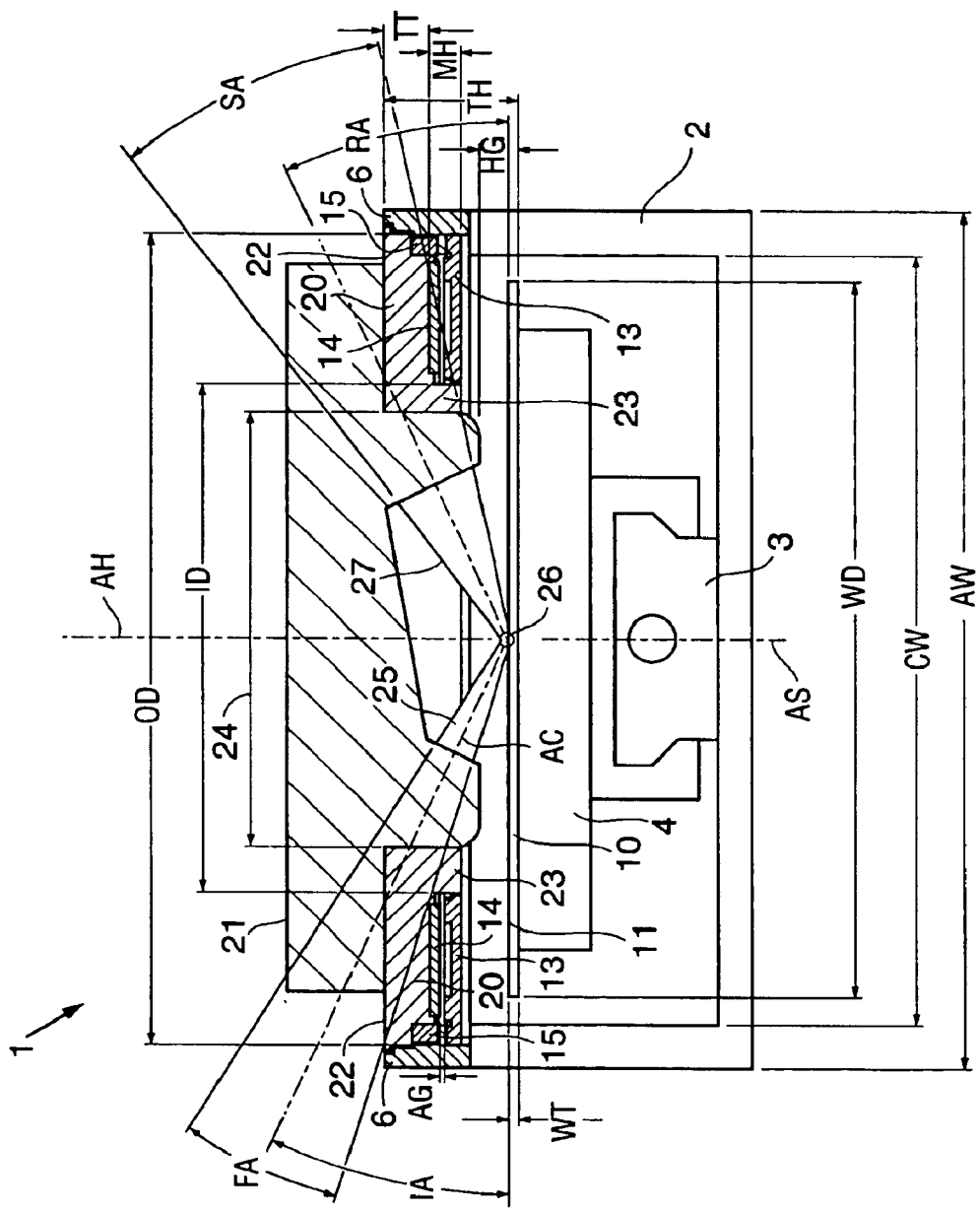
FIG. 4 shows the exemplary apparatus of FIG. 3 in front view for the purpose of general understanding of the spatial configuration of the apparatus.

In the preferred embodiment, the present invention is utilized for performing directional reflectance measurement of a wafer 10 (see FIGS. 3–6) within a minimal footprint of the apparatus 1 (see FIGS. 3, 4). During directional reflectance measurement, surface features 12a, 12b (see FIGS. 3, 5, 6) have to be accessed by a probe beam 25 (see FIGS. 3–6) in an impinging direction that is oriented in conjunction with the orientation of the surface features 12a, 12b. The features 12a, 12b may be located anywhere on the wafer surface 11 and may need to be positioned in a specific orientation for measurement. Thus, in order to perform directional reflectance measurement on essentially the entire wafer surface 11, the direction of the probe beam 25 is rotated in combination with a positioning movement of the wafer 10.

For accessing a measurement area of a wafer 10, for directional reflectance measurement, three movement qualities need to be provided. In the prior art, three motion stages were used to provide two linear movements and one rotational movement. This approach resulted in a wafer travel envelope LE that was about four times the wafer size. In the subject invention, the three movement qualities are defined by a single linear movement preferably induced by a stage, and two rotational movements, one from a stage and one created by rotating the direction in which the probe beam impinges upon the wafer. By the arrangement, the travel envelope TE (see FIGS. 3, 5, 6) is consequently only the wafer size plus an area defined by the wafer radius times the wafer diameter, which sums up to about only 1.57 times the wafer size. Even with this substantially reduced travel envelope, the structures on the wafer can be measured in the preferred orientation.

Consistent beam configuration is important for a precise measurement. The present invention addresses the requirements for consistent beam configuration by preferably making the entire optical assembly 21 rotatable. Rotating the entire optical assembly 21 raises demands for smooth actuation in order to prevent vibrations that would affect the operation of the optical assembly 21.

Figure 6:
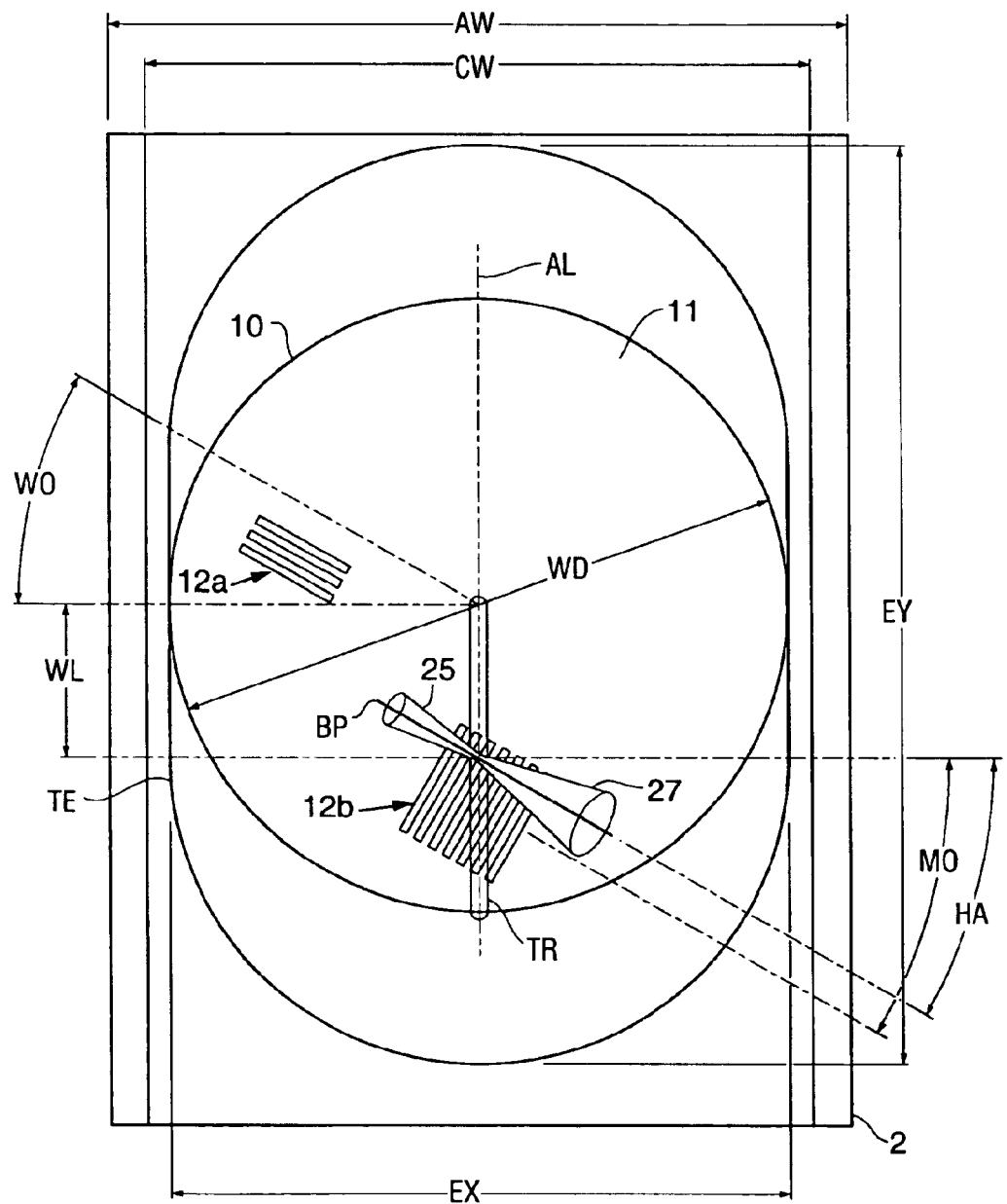
FIG. 6 shows a top down view of FIG. 5.
Figure 7:
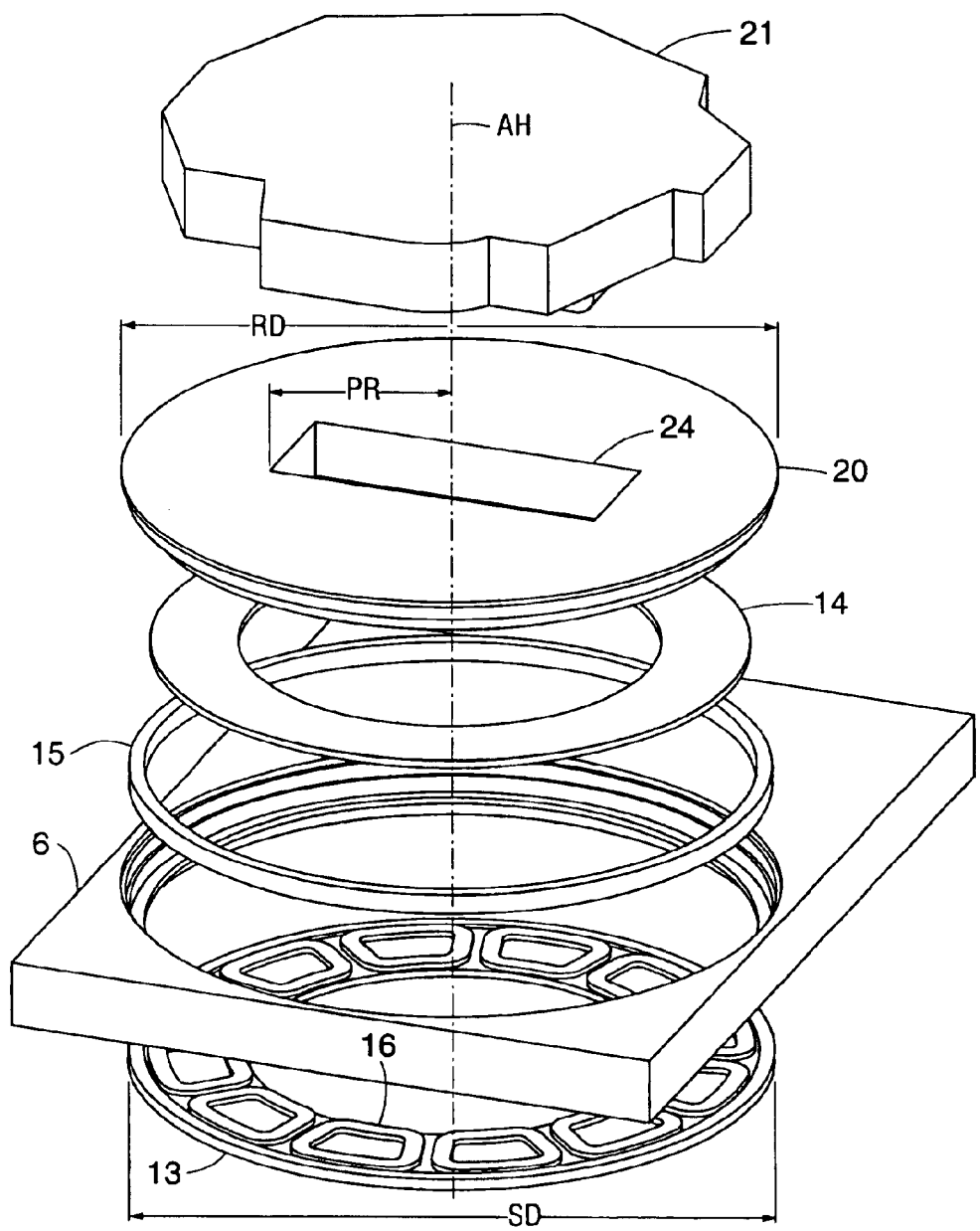
FIG. 7 shows a simplified exploded view of the top portion of the apparatus of FIG. 3.

In order to accommodate for a smooth yet quick and precise actuation of the relatively heavy and bulky optical assembly 21, a specifically configured direct driver motor is embedded between the optical assembly 21 and the immovable portion of the apparatus 1. Further more, the driver motor is configured to directly actuate the optical assembly 21. The driver motor provides the torque necessary to directly accelerate and decelerate the optical assembly 21 within a short period. This is accomplished by building the driver motor with a unique ring shape where the coils 16 (see FIG. 7) responsible for creating the magnetic forces are at a maximum distance from the head axis AH. Thus, for a given magnetic force and energy consumption, the motor provides a relatively high torque compared to conventional driver motors with similar power consumption. The ring shape of the driver motor also provides space for optical components in the direct proximity of the wafer surface 11 such that the probe beam 25 and a resulting reflected beam 27 (see FIGS. 3–6) may be properly provided and received.

Specific Elements

According to FIG. 3, an ellipsometric apparatus 1 of the preferred embodiment has a base 2 on which a linear stage 3 and an immovable top 6 are mounted. The linear stage 3 carries a rotating stage 4 configured to receive and hold a sample wafer 10. Embedded in the immovable top 6 is a bearing 15 (see also FIG. 7), which holds a rotating optics plate 20 rotatable within the immovable top 6. The rotating optics plate 20 carries an optical assembly 21. The optical assembly 21 is configured in accordance with the known techniques of ellipsometry to produce a probe beam 25 impinging a wafer surface 11 within a focal spot 26. As a result, a reflected beam 27 carries away from the focal spot 26 reflectance information, which is captured and recognized within the optical assembly 21. On the bottom side of the rotating optics plate 6 is attached a rotor 14 (see also FIG. 7), which defines in conjunction with a stator 13 (see also FIG. 7) a ring shaped driver motor that drives the rotating optics plate 6 and consequently the optical assembly 21. The stator 13 is embedded in and attached on the immovable top 6. The rotating optics plate 20, the rotor 14 and the optical assembly 21 rotate around a head axis AH, which is immobile within the apparatus 1. The rotating stage 4 and the wafer 10 rotate around a stage axis AS, which moves in direction of a linear axis AL of the linear stage 3. In the preferred embodiment, the focal spot 26 is essentially coaxial with the head axis AH Referring to FIG. 4, a minimal gap height HG is maintained between the rotating stage 4 and elements of the top like, for example, a central portion of the optical assembly 21. The gap height HG is predetermined in order to provide sufficient space for loading and unloading the wafer 10 on the rotating stage 4. The central portion protrudes through the rotating optics plate 6 and includes well-known optical components in proximity of the probe beam 25 and reflected beam 27. Such adjacent optical components are for example, a polarizer, a lens unit, a rotating waveplate, and/or a parabolic mirror as they are well known to those skilled in the art.

A number of optical components of the optical assembly 21 are positioned and fixed on a planar top surface 22 of the rotating optics plate 6. The rotating optics plate 6 has a top height TH being at a minimum as well.

The rotating stage 4 may have a vertical adjustment range as it is known for precisely position the wafer surface 11 within the focal spot 26 in direction of the stage axis SA. In that case, the heights HG and TH may be defined relative to a vertical reference position of the rotating stage 4.

A beam geometry of the probe beam 25 and the reflected beam 27 includes, for example, an impinging angle (angle of incidence) IA, a focus angle FA, a reflection angle (angle of reflection) RA and spreading angle SA. Impinging angle IA and reflection angle RA relate to center axes of the probe beam 25 and the reflected beam 27. The beam geometry in conjunction with the gap height HG minus a wafer thickness WT influences the size and position of the adjacent optical components and consequently a shape and a maximal radial extension PR (see FIG. 7) of the central opening 24 (see also FIG. 7). The central opening 24 of the rotating optics plate 6 provides the necessary space for the adjacent optical components and for the inclining and declining beam paths in the central portion of the optical assembly 21. In the preferred embodiment where the impinging angle IA is in the range of 25 degrees, the focus angle FA is in the range of 10 degrees, the reflection angle RA is in the range of 25 degrees, the spreading angle SA is in the range of ten degrees.

An outside diameter OD is provided by the immovable top 6 within which the rotating optics plate 20, the bearing 15, the rotor 14 and the stator 13 are positioned. The outside diameter OD depends on the apparatus width AW such that sufficient space remains for the immovable top 6. The apparatus width AW in turn is dependent on the clearance width CW necessary to load and unload the wafer 10 having a wafer diameter W1 such that sufficient space remains for the walls and other known elements of the base 2. For a wafer diameter WD of about 300 mm, the clearance width CD is about 305 mm.

An inside diameter ID is provided by the rotating optics plate 6 and is selected in conjunction with the central opening 24 and to provide eventual additional space for a central flange 23 of the rotating optics plate 6. The central flange 23 may provide additional stiffness to the rotating optics plate 6 and/or may assist to position and hold adjacent optical components and/or the rotor 14.

The stator 13 and the rotor 14 fit within an envelope defined by the diameters ID, OD, the gap height HG and the top height TH minus the top thickness TT, which is selected to provide sufficient stiffness for the optical assembly 21. In the preferred embodiment, the stator 13 has a stator diameter SD (see FIG. 5) of about 14.4 in and the rotor 14 has a rotor diameter RD (see FIG. 5) of about 13.8 in. An axial gap AG between rotor 14 and stator 13 is about 0.15 in. The ring shaped driver motor is concentrically assembled relative to the head axis AH with the rotor and stator sections being in a significant distance to the head axis AH. Consequently, a high torque is provided within a minimum occupied space and minimal power consumption.

Figure 5:
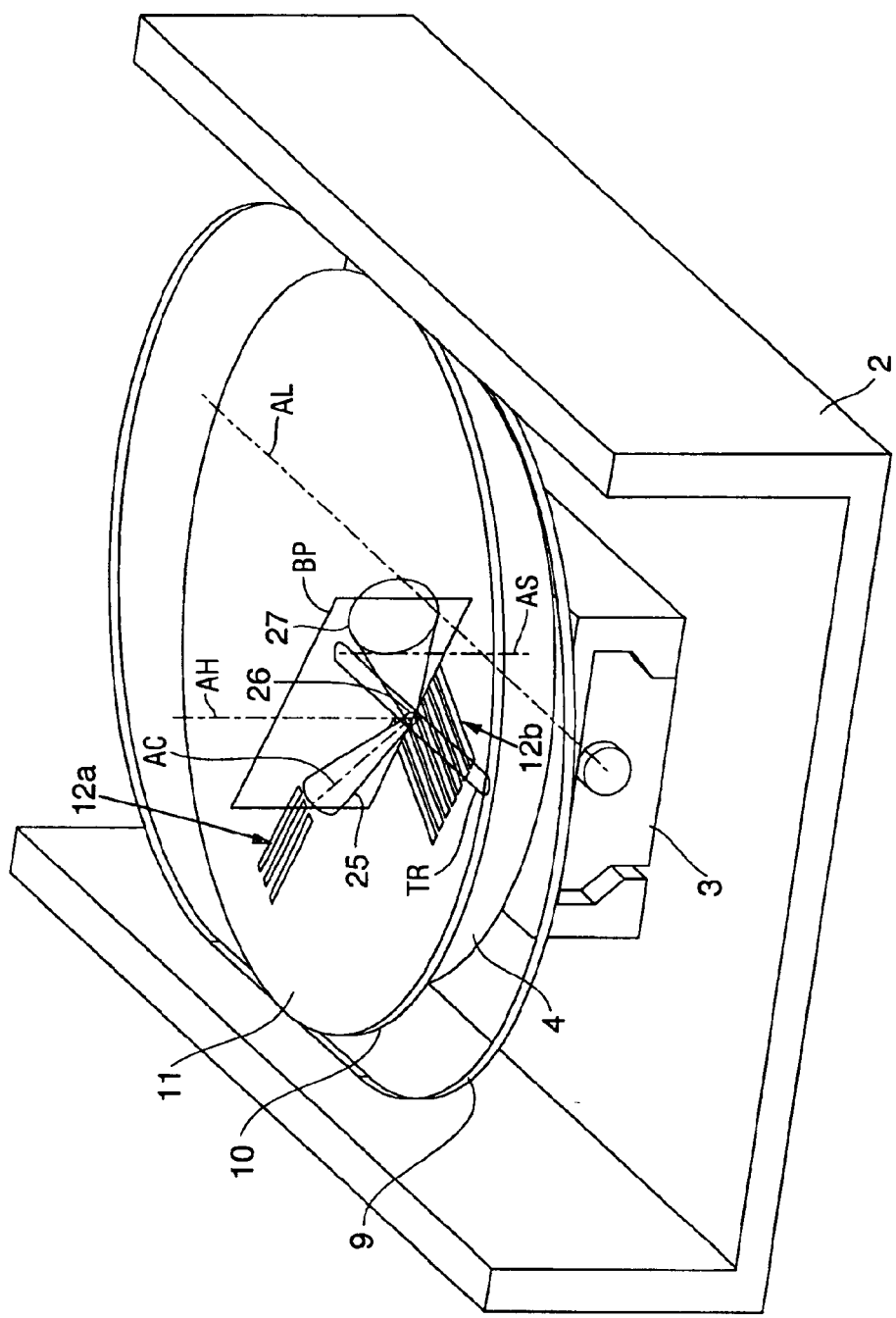
FIG. 5 shows the perspective view of FIG. 3 having the top portion removed.

In the preferred embodiment, the stator 13 features coils 16 exemplary illustrated in FIG. 5 and the rotor 14 features permanent magnets. Parts accelerated by the driver motor include mainly the rotating optics plate 20, the optical assembly 21 and the rotor 14. In the preferred embodiment, the inertia of the accelerated parts is about 3.6 Lb-in-$s^2$. The driver motor is configured to accelerate and decelerate the inertia at a rate of about 0.25 rev/$s^2$ and is preferably driven by an encoder based commutation scheme drive having a 24-48 VDC bus with phase current amplitudes of less than 3 Amps. The driver motor has preferably a duty cycle of approximately 25%. The duty cycle is the percentage of the motor's operating time within a given measurement cycle of the wafer 10.

The design of the rotating optics plate is intended to minimize tilt and wobble. In initial experiments, the tilt of the plate as a result of rotation was kept below 0.01 degrees.

Figure 1:
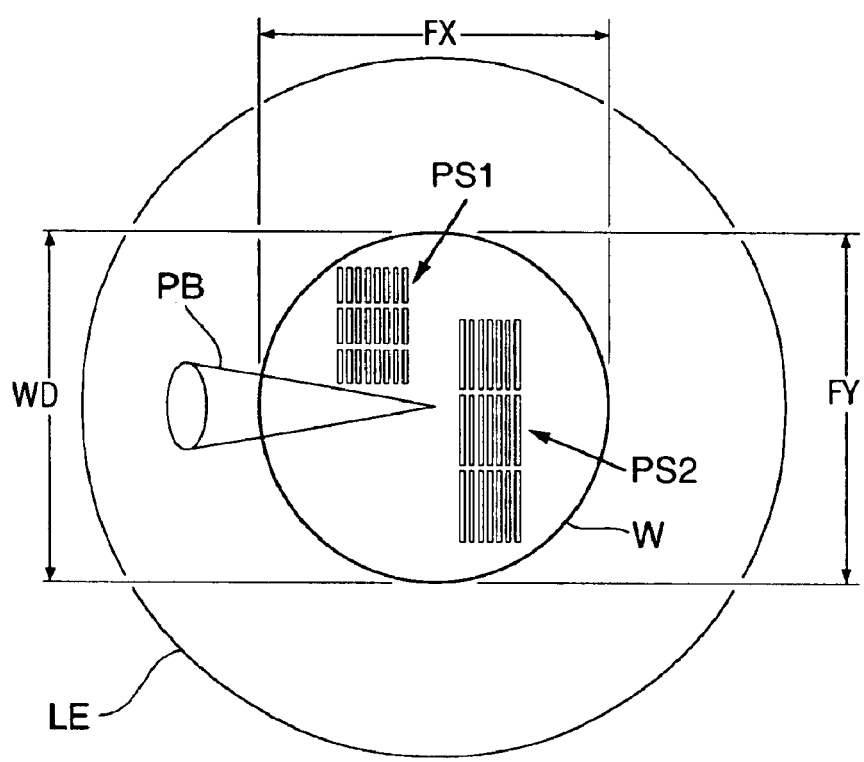
FIG. 1 shows a simplified scheme of a prior art positioning system of an ellipsometer system where two linear stages move a wafer in ranges about equal the wafer diameter.
Figure 2A:
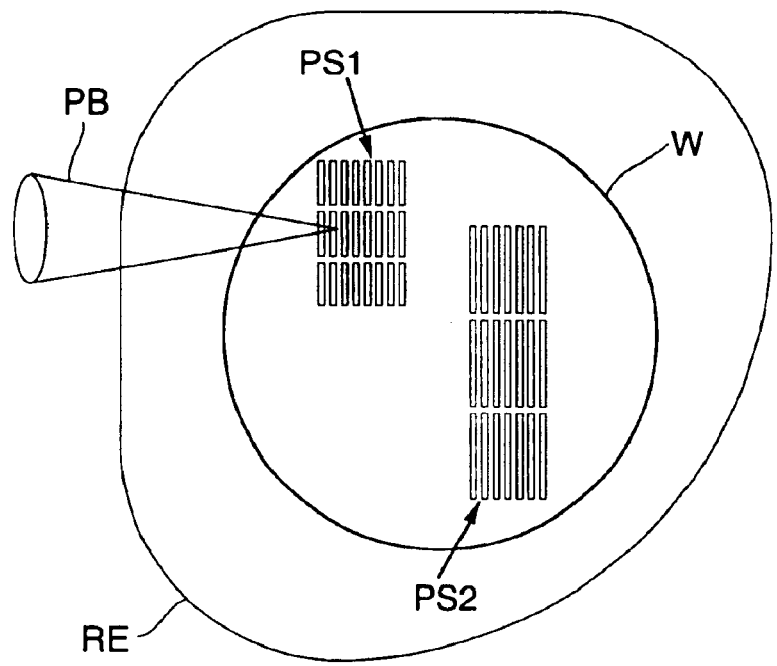
FIGS. 2A and 2B show simplified schemes of a prior art positioning system of an ellipsometer system where two linear stages move a wafer in ranges about half the wafer diameter. In such prior art positioning system the probe beam is limited to reflectance measurements where the beam direction is irrelevant relative to measured features of the wafer.
Figure 2B:
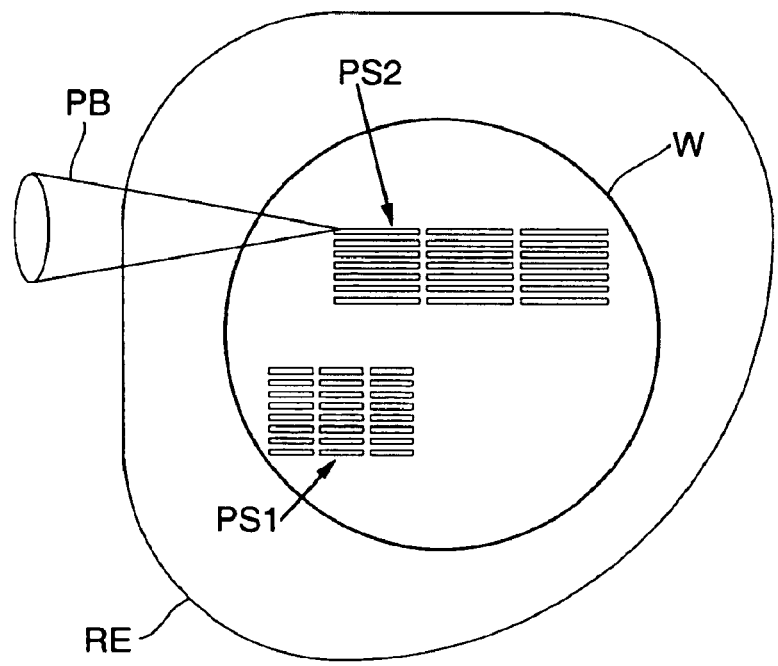

As shown in FIG. 2, a travel range TR is defined by the linear stage 3. The travel range TR is a lengthy area accessible by focal spot 26 by operating the linear stage 3. The travel range TR is a fictive and global entity introduced for the purpose of general understanding. It can be imagined as being drawn by the focal spot 26 on a fictive element directly attached to the linear stage 3 moving along a linear axis AL of it. The rotating stage 4 is thereby positioned with its stage axis AS on the linear stage 3 such that a measurement area of the wafer 10 may be rotated and brought within the travel range TR.

The wafer 10, which is preferably concentrically fixed on the rotating stage 3 occupies a travel envelope TE within the apparatus 1. The travel envelope TE is a fictive boundary within which the wafer 10 may interfere with objects while fixed on the rotating stage 3 and moved by the linear stage 3 and/or the rotating stage 4. In the preferred embodiment, where the single linear stage 3 is utilized, the travel envelope TE has an envelope width EX (see FIG. 6) essentially equal to the wafer diameter WD and an envelope length EY (see FIG. 6) that is essentially equal to the wafer diameter WD plus the linear travel range TR.

In the preferred embodiment, the axes AH, AS define together with the linear axis AL a common plane whereby the travel range TR is kept to a minimum. Hence, in the case where the measurement area is essentially the same as the wafer surface 11, the travel range TR may be as small as the radius of the wafer surface 11. It is noted that the scope of the invention includes embodiments where either one or both of the axes AH, AS are not in plane with the linear axis AL. The scope of the invention further includes embodiments where the head axis AH is not in plane with the stage axis AS.

Measurement areas may include surface features 12a, 12b placed on the wafer surface 11. In the preferred embodiment where a directional reflectance measurement is performed by the apparatus 1, the surface features 12a, 12b are considered in the following as direction sensitive measurement features that occupy areas on the wafer surface 11 and are predetermined to be impinged by the probe beam 25 within a measurement orientation MO (see FIG. 6).

The rotating optics plate allows the direction at which the beam impinges upon the sample to be rotated. For ease of understanding, the direction of the beam can be defined in terms of a beam plane BP in which both the incident beam 25 and the specularly reflected beam 27 lie (see FIGS. 5 and 6). This definition is idealized and assumes a clean, planar sample where the angle of incidence equals the angle of reflection. This definition, as it is used in the specification and claims, is merely for convenience and is intended to help distinguish the invention from devices which changed the angle of incidence of the probe beam using some angular rotational mechanism. It should be understand that in actual operation, the reflected probe beam could be scattered so that no beam plane would be defined. In the preferred embodiment, the axis of rotation AH of the optics plate intersects with the focal spot of the probe beam on the sample.

In FIGS. 3 and 5, the surface feature 12b is rotated within the travel range TR. For each measurement location within the surface feature 12b, the wafer 10 is rotated by the rotating stage 3 into a distinct wafer orientation WO and linearly moved into a distinct linear wafer position WL. For each measurement location, the surface features 12a, 12b have a distinct measurement orientation MO. In order to perform the directional reflectance measurement at the measurement location, the driver motor rotates the optical assembly 21 around a distinct head angle HA such that the impinging direction is essentially collinear with the measurement orientation MO. In FIG. 5, the angles WO, MO, HA are exemplary illustrated relative to a horizontal reference orientation. Such reference orientation may be any orientation separately and/or combined defined for the wafer 10 and the optical assembly 21. The angles WO, MO, HA and the wafer position WL are calculated by a processor, which concurrently operates the stages 3,4 and the driver motor.

The rotating optics plate 20 may further provide on its circumference an indexing pattern, which in conjunction with a sensor placed on the immovable portion 6 provides information about angular movement and/or position of the rotating optics plate 6. The scope of the invention includes embodiments, where other well known means for retrieving angular position and/or movement information are utilized.

The scope of the invention is not limited to specific configurations of the optical assembly 21. Moreover, the present invention includes embodiments, where a measurement assembly is substituted and/or added to the optical assembly 21. Such a measurement assembly may be, for example, a well known focusing system or a calibration system. A pattern recognition system might also be used.

The scope of the invention is not limited to a specific configuration of the rotating stage 4, the linear stage 3, and/or the rotating optics plate 20. For example, the rotating ranges of the rotating optics plate 20 and the rotating stage 4 may be 180° and the travel range TR may be about equal the wafer diameter WD.

In addition, the order of the stacking of the stages could be varied.

Another possibility is to use two ½ travel linear stages (½X and ½Y) in combination with a rotary stage. In this case, full access to the sample could be achieved if the rotary stage was only capable of 90 degree rotation.

In the preferred embodiment, the bearing 15 is a high precision ball bearing. Nevertheless, the scope of the invention includes embodiments, in which the bearing is configured to primarily provide high precision positioning in varying angular orientations when the rotating optics plate 20 is not moving. This may be accomplished for example by an actuating bearing that lifts the rotating optics plate 20 during rotation where precision demands are secondary. Once the rotating optics plate 20 is brought into a predetermined orientation, the actuating bearing may lower the rotating optics plate 20 into a corresponding fit with the immovable top 20. Such actuating bearing may be combined with the driver motor in a fashion, that a magnetic force produced between the rotor 14 and stator 13 may be utilized for lifting the rotating optics plate 20 from its corresponding fit.

Figure 8:
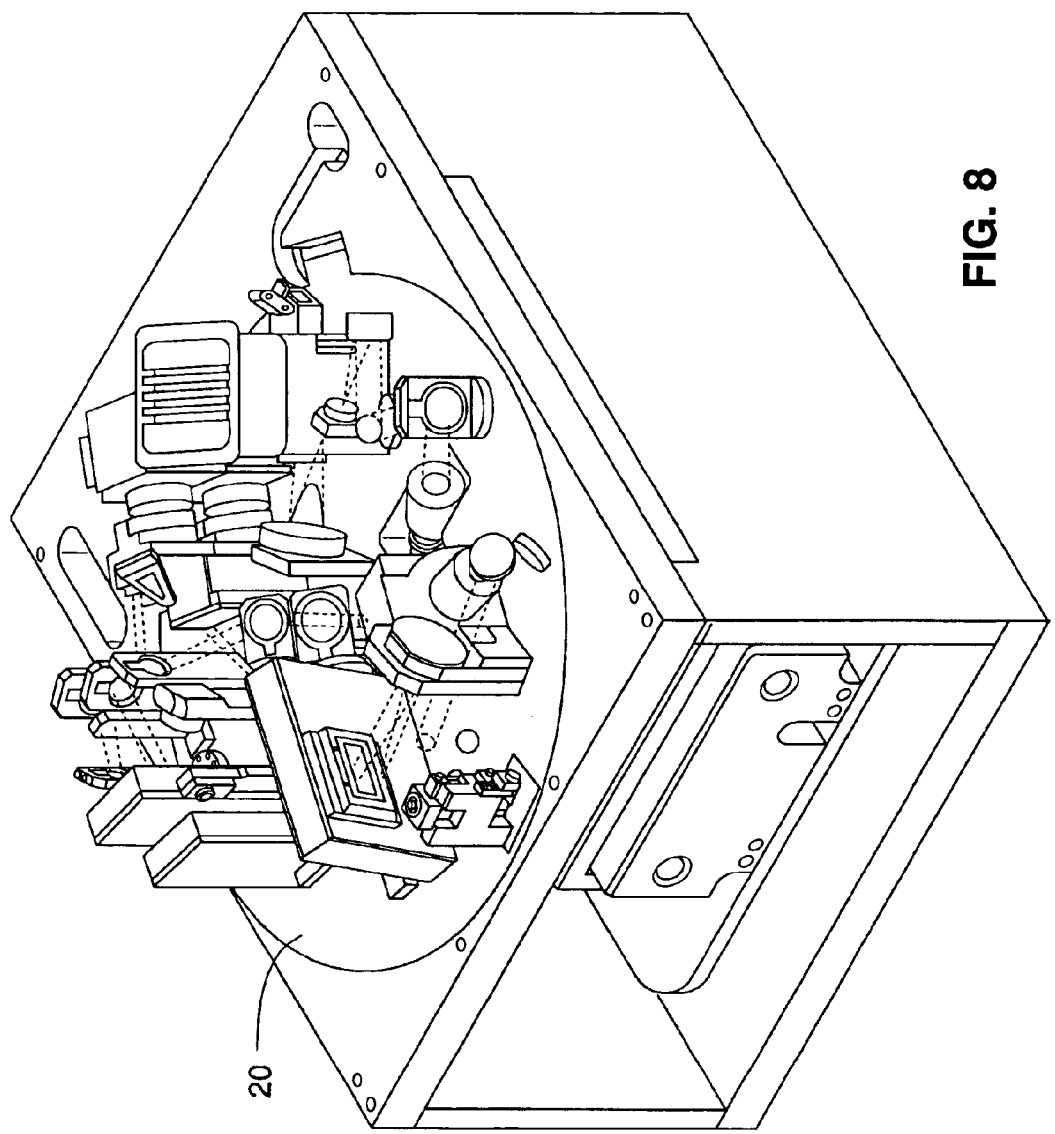
FIG. 8 is a perspective view of the optical elements in a preferred embodiment capable of spectroscopic ellipsometric measurements.
Figure 9:
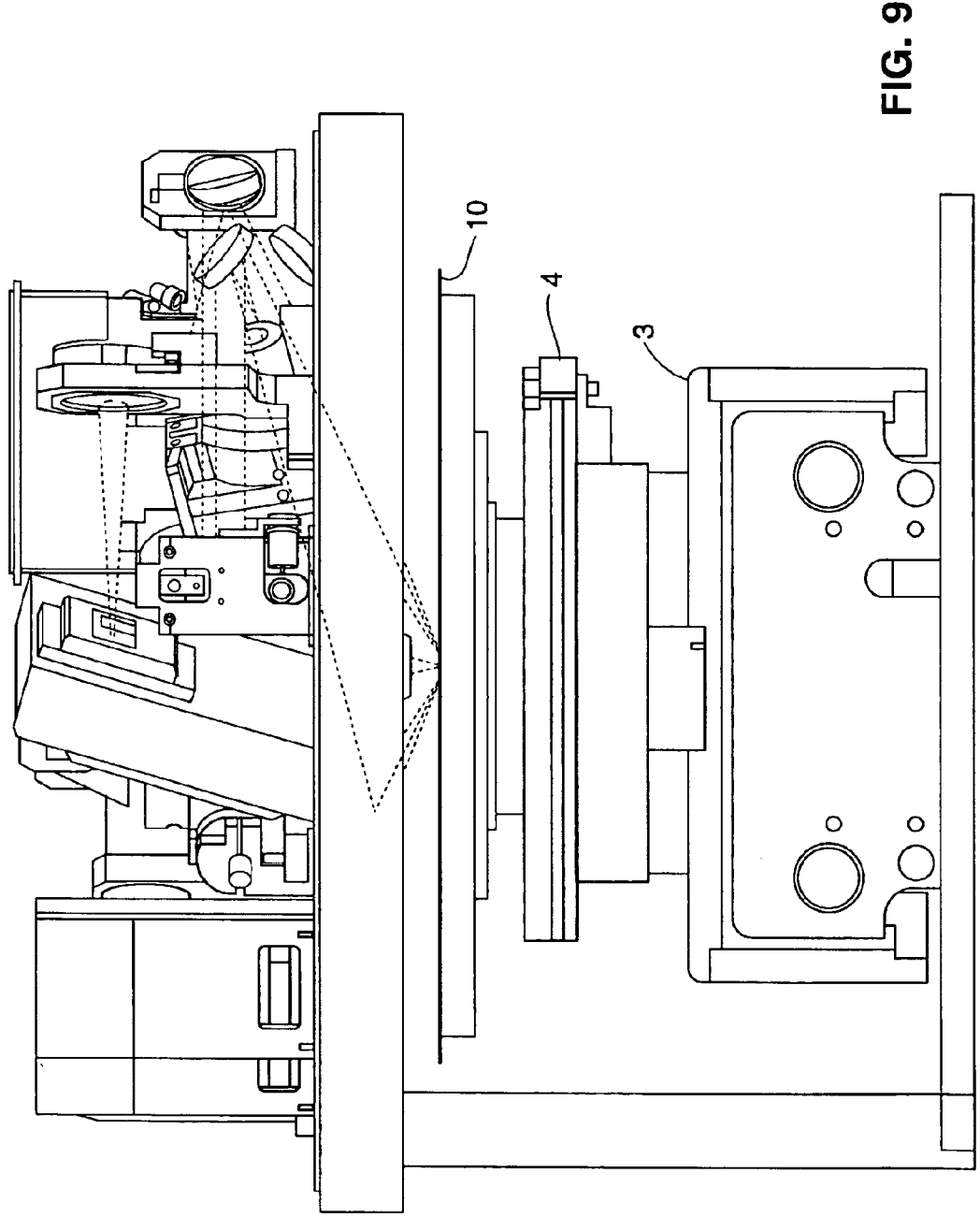
FIG. 9 is a side view of the embodiment shown in FIG. 8.

FIGS. 8 and 9 illustrate one preferred embodiment capable of obtaining spectroscopic ellipsometric measurements. This particular embodiment is a rotating compensator ellipsometer of the type described in U.S. Pat. Nos. 5,973,787 and 6,278,519, cited above. As can be seen, all of the main optical components of the system are mounted on the rotating optics plate 20. These elements include a polychromatic or white light source 40 for generating a broadband probe beam. The light source can, for example, include one or more tungsten, deuterium and xenon bulbs. A polarizer 42 is provided for polarizing the beam. A lens system 44 focuses the probe beam on the sample. The reflected beam is collected and passed through a rotating compensator 46 and another polarizer 48. The beam is then directed to a spectrometer 50 which includes a grating for dispersing the light and an array photodetector for generating output signals as a function of wavelength.

Figure 10:
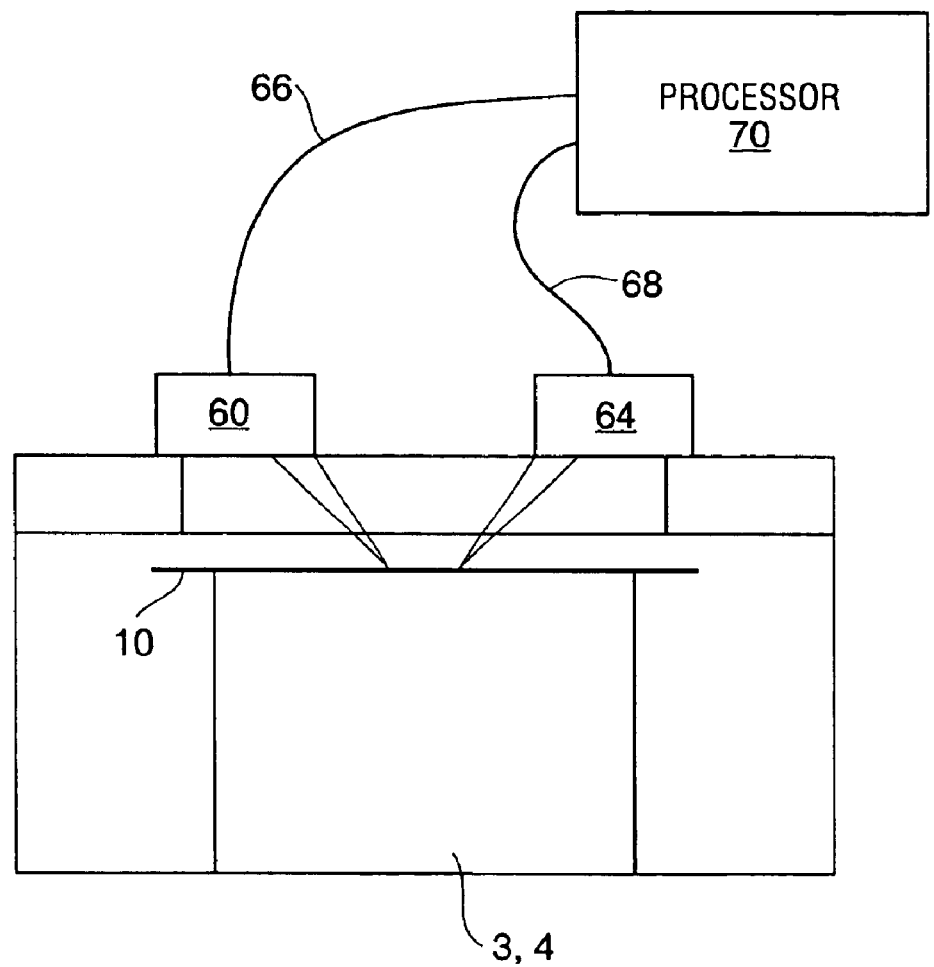
FIG. 10 is a schematic simplified diagram of the embodiment of FIG. 8 incorporated into a system.

All the elements recited above are rotated on plate 20. FIG. 10 schematically indicates the electrical connections between the measurement optics and the system processor 70. In FIG. 10, the probe beam generating and focusing optics are shown generally as 60 while the reflected probe beam collection and detection optics are shown as 64. Electrical wires 66 and 68 are shown connecting the generation and collection optics to a processor 70. Processor 70 is responsible for controlling the operation of the system and for collecting data from the detection optics. Analysis of the sample can be performed by the processor or in a separate processor either on board the tool, connected through a network or off-line. Processor 70 also controls the motor driving the optics plate as well as the stages (shown generically as 3,4).

Since the optics plate must be electrically connected to the processor, the rotation of the optics plate should be limited to 360 degrees so that the wires 60 and 64 do not become twisted. It should also be understand that in the actual embodiment, wires 60 and 64 are actually multiple wires connecting the various optical elements necessary to perform measurements including, for example, reference detectors (not shown). Determination of the characteristics of the wafer based on the collected data is carried out in a conventional manner as well known to those skilled in the art.

In the embodiment illustrated in FIGS. 8 to 10, the entire measurement assembly is fixed to the rotating optics plate 20. Nevertheless, the scope of the present invention includes embodiments, where some optical components are not assembled on the rotating optics plate 20. For example, it would be possible to use an optical fiber to deliver light from a remote light source to the focusing optics on the plate 20. Similarly, it would be possible to use an optical fiber to transport light reflected off the sample to a remote detector (spectrometer).

The scope of the invention is also not limited to a particular impinging angle IA. Moreover, embodiments are within the scope of the invention, where the orientation of the head axis AH and/or the impinging angle IA is/are selected such that the head axis AH may be within the probe beam 25. Thereby, the impinging direction of the probe beam 25 is still independent of any eventual device for rotating the wafer 10.

Also, the scope of the invention includes embodiments, where the impinging direction and/or the beam plane BP are not solely defined by the rotational orientation of the optical assembly 21. For example, the impinging direction may be adjusted without inducing a rotation to the optical assembly. Also, the scope of the invention includes embodiments, where the focal spot 26 may be adjusted relative to the wafer 10 without operating one or both of the stages 3, 4. Impinging direction and/or focus spot 26 may be adjusted as part of a well-known calibration process or a focusing process. Additional mechanical features and/or optical features may be assembled on the rotating optics plate 20 to accomplish these tasks.

Accordingly, the scope of the invention described in the specification above is set forth by the following claims and their legal equivalent:

What is claimed is:

1. A measurement apparatus for examining features on a sample, comprising:

a base including a moveable stage for supporting the sample, and further including a measurement assembly support member positioned a distance from the moveable stage;

a rotatable measurement plate positioned at least partially within an opening in the measurement assembly support member, the rotatable measurement plate capable of supporting a measurement assembly thereon;

a bearing positioned between the measurement assembly support member and the rotatable measurement plate allowing the rotatable measurement plate to rotate with respect to the measurement assembly support member; and a ring-shaped driver motor coupled to the measurement assembly support member and the rotatable measurement plate, the ring-shaped driver motor capable of rotating the rotatable measurement plate with respect to the measurement assembly support member in order to adjust an orientation of the measurement assembly with respect to the sample on the moveable stage.

2. A measurement apparatus according to claim 1, wherein:

the moveable stage is a linear translation stage capable of translating the sample along a single axis of motion that is substantially perpendicular to an axis of rotation of the rotatable measurement plate.

3. A measurement apparatus according to claim 2, wherein:

the moveable stage is further capable of rotating the sample, whereby any point on the sample can be measured by the measurement assembly through a rotation of the sample and a translation of the sample along the single axis of motion.

4. A measurement apparatus according to claim 1, wherein:

the measurement assembly is an optical assembly configured to direct a measurement beam off a measurement spot on the sample and detect a reflected portion of the measurement beam.

5. A measurement apparatus according to claim 1, wherein:

the ring-shaped driver motor includes a ring-shaped rotor coupled to the rotatable measurement plate and a ring-shaped stator coupled to the measurement assembly support member.

6. A measurement apparatus according to claim 5, wherein:
the ring-shaped driver motor is capable of rotating the rotor, rotatable measurement plate, and measurement assembly about a rotational axis substantially orthogonal to a plane of the sample.

7. A measurement apparatus according to claim 5, wherein:
the measurement assembly utilizes a measurement spot that is coaxial with the rotational axis of the ring-shaped driver motor.

8. A measurement apparatus according to claim 5, wherein:
the stator of the ring-shaped driver motor includes a plurality of coils and the rotor includes a plurality of permanent magnets for causing a rotation of the rotor with respect to the stator.

9. A measurement apparatus according to claim 5, wherein:
the ring-shaped driver motor is configured to accelerate and decelerate the rotation of the rotatable measurement plate at a rate of about 0.25 revolutions per second$^2$.

10. A measurement apparatus according to claim 5, wherein:
the ring-shaped driver motor is driven by an encoder based commutation scheme drive having a 24–48 VDC bus with phase current amplitudes of less than 3 Amps.

11. A measurement apparatus according to claim 5, wherein:
the ring-shape driver motor has a duty cycle of approximately 25%.

12. A measurement apparatus according to claim 5, wherein:
the rotatable measurement plate includes an indexing pattern near a circumference of the rotatable measurement plate, and the measurement assembly support member includes an indexing sensor for detecting the indexing pattern, whereby information can be obtained about at least one of the angular movement and angular position of the rotatable measurement plate.

13. A measurement apparatus according to claim 1, wherein:
the rotatable measurement plate includes a central flange for engaging the rotor.

14. A measurement apparatus according to claim 1, wherein:
the rotatable measurement plate has a central opening therein, whereby the measurement assembly can direct a measurement beam off a measurement spot on the sample and detect a reflected portion of the measurement beam.

15. A measurement apparatus according to claim 1, wherein:
the measurement assembly is an optical assembly including optical components selected from the group consisting of light sources, light detectors, polarizers, lens units, rotating waveplate, and parabolic mirrors.

16. A measurement apparatus according to claim 1, wherein:
the ring-shaped driver motor is concentrically assembled relative to a rotational axis of the rotatable measurement plate.

17. A measurement apparatus according to claim 1, wherein:
a tilt of the rotatable measurement plate with respect to the sample as a result of rotation by the ring-shaped driver motor is less than 0.01 degrees.

18. A measurement apparatus according to claim 1, wherein:
rotation of the rotatable measurement plate changes a direction at which a measurement beam generated by the measurement apparatus impinges upon the sample.

19. A measurement apparatus according to claim 18, wherein:
the direction at which the measurement beam impinges upon the sample is rotated to be substantially collinear with a feature on the sample.

20. A measurement apparatus according to claim 1, wherein:
the measurement assembly includes a pattern recognition system.

21. A measurement apparatus according to claim 1, wherein:
the bearing is a high precision ball bearing.

22. A measurement apparatus according to claim 1, wherein:
the bearing is an actuating bearing capable of lifting the rotatable measurement plate during rotation.

23. A measurement apparatus according to claim 1, wherein:
the measurement apparatus includes a light source for generating a measurement beam and a lens system for focusing the measurement beam through a central opening in the rotatable measurement plate and onto a measurement spot on the sample.

24. A measurement apparatus according to claim 23, wherein:
the measurement apparatus further includes a detector assembly for capturing a reflected portion of the measurement beam.

25. A measurement apparatus according to claim 24, wherein:
the detector assembly includes one of a spectrometer and an ellipsometer.

26. A measurement apparatus according to claim 23, wherein:
at least some of the elements of the measurement assembly are contained within the central opening of the rotatable measurement plate.

27. A measurement apparatus according to claim 1, further comprising:
a processor for controlling the ring-shaped driver motor.

28. A measurement apparatus according to claim 27, wherein:
the processor is further capable of controlling the moveable stage.

29. A measurement apparatus according to claim 1, wherein:
the ring-shaped driver motor directly drives the rotatable measurement plate without any reduction gear.

30. An optical apparatus for evaluating features on a wafer, comprising:
an optical assembly for directing and focusing a probe beam on the wafer at a predetermined angle of incidence so that the probe beam is reflected therefrom, the optical assembly further including a detector assembly for measuring a reflected portion of the probe beam;

a base including a measurement assembly support member and a rotatable measurement plate positioned at least partially within an opening in the measurement assembly support member, the rotatable measurement plate capable of supporting the optical assembly; and a ring-shaped driver motor coupled to the measurement assembly support member and the rotatable measurement plate, the ring-shaped driver motor capable of rotating the rotatable measurement plate with respect to the measurement assembly support member in order to adjust an orientation of the optical assembly with respect to the wafer.

31. An optical apparatus according to claim 30, further comprising:

a bearing positioned between the measurement assembly support member and the rotatable measurement plate in order to allow the rotatable measurement plate to rotate with respect to the measurement assembly support member.

32. A measurement apparatus according to claim 30, wherein:

the ring-shaped driver motor includes a ring-shaped rotor coupled to the rotatable measurement plate and a ring-shaped stator coupled to the measurement assembly support member.

33. A measurement apparatus according to claim 32, wherein:

the ring-shaped driver motor is capable of rotating the rotor, rotatable measurement plate, and measurement assembly about a rotational axis.

34. A measurement apparatus according to claim 32, wherein:

the stator of the ring-shaped driver motor includes a plurality of coils and the rotor includes a plurality of permanent magnets for causing a rotation of the rotor with respect to the stator.

35. A measurement apparatus according to claim 30, wherein:

rotation of the rotatable measurement plate changes a direction at which the probe beam generated by the optical assembly impinges upon the wafer.

36. A measurement apparatus according to claim 35, wherein:

the direction at which the probe beam impinges upon the wafer is rotated to be substantially collinear with a feature on the wafer to be measured.

37. An optical apparatus for evaluating features on a wafer, comprising:

a base including a moveable stage for supporting the sample, the moveable stage capable translating and rotating the wafer, the base further including a measurement assembly support member positioned a distance from, and substantially parallel to, the moveable stage;

an optical assembly for directing and focusing a probe beam to a measurement spot on the wafer at a predetermined angle of incidence so that the probe beam is reflected therefrom, the optical assembly further including a detector assembly for measuring a reflected portion of the probe beam;

a rotatable measurement plate positioned at least partially within an opening in the measurement assembly support member, the rotatable measurement plate supporting the optical assembly and capable of rotating the optical assembly about a rotational axis that is collinear with the measurement spot;

a ring-shaped driver motor coupled to the measurement assembly support member and the rotatable measurement plate, the ring-shaped driver motor capable of rotating the rotatable measurement plate with respect to the measurement assembly support member in order to adjust an orientation of the optical assembly with respect to the wafer; and a processor for controlling the ring-shaped drive motor and moveable stage in order to position a feature of the wafer within the measurement spot and adjust a direction at which the probe beam, generated by the optical assembly, impinges upon the wafer.

38. An optical apparatus according to claim 37, further comprising:

a bearing positioned between the measurement assembly support member and the rotatable measurement plate in order to allow the rotatable measurement plate to rotate with respect to the measurement assembly support member.

39. A measurement apparatus according to claim 37, wherein: the ring-shaped driver motor includes a ring-shaped rotor coupled to the rotatable measurement plate and a ring-shaped stator coupled to the measurement assembly support member.

40. A measurement apparatus according to claim 32, wherein:

the stator of the ring-shaped driver motor includes a plurality of coils and the rotor includes a plurality of permanent magnets for causing a rotation of the rotor with respect to the stator.

* * * * *